United States Patent
Zilioli

(10) Patent No.: US 7,603,888 B2
(45) Date of Patent: Oct. 20, 2009

(54) AUTOMATIC SAMPLER ASSOCIABLE WITH CHROMATOGRAPHIC ANALYSIS INSTRUMENTS

(75) Inventor: Giacinto Zilioli, Rodano (IT)

(73) Assignee: Thermo Electron S.p.A., Rodano (MI) (IT)

( * ) Notice: Subject to any disclaimer, the term of this patent is extended or adjusted under 35 U.S.C. 154(b) by 206 days.

(21) Appl. No.: 10/591,840

(22) PCT Filed: Feb. 22, 2005

(86) PCT No.: PCT/IB2005/000441

§ 371 (c)(1),
(2), (4) Date: Dec. 1, 2006

(87) PCT Pub. No.: WO2005/085834

PCT Pub. Date: Sep. 15, 2005

(65) Prior Publication Data
US 2008/0156119 A1   Jul. 3, 2008

(30) Foreign Application Priority Data
Mar. 3, 2004   (IT)   .......................... MI2004A0399

(51) Int. Cl.
*G01N 30/24* (2006.01)
(52) U.S. Cl. .................. 73/23.41; 73/23.36; 73/61.55; 73/61.56

(58) Field of Classification Search ................ 73/23.36, 73/23.41, 61.55, 61.56
See application file for complete search history.

(56) References Cited

U.S. PATENT DOCUMENTS

| 5,668,735 A | * | 9/1997 | Dominguez et al. ........... 702/24 |
| 2001/0027949 A1 | | 10/2001 | Safir et al. |
| 2002/0068366 A1 | * | 6/2002 | LaDine et al. ............... 436/518 |

FOREIGN PATENT DOCUMENTS

| JP | 2002-340876 A | * | 11/2002 |
| WO | 01/84143 A | | 11/2001 |

OTHER PUBLICATIONS

International Search Report of PCT/IB2005/000441, mailed Jun. 14, 2005.
ASI-100™ and ASI-100T™ Autosamplers, Online!—2002, pp. 1-6, XP002329480 Dionex, Retrieved from the Internet: URL:www.dionex.com.

* cited by examiner

*Primary Examiner*—Daniel S Larkin
(74) *Attorney, Agent, or Firm*—Nixon & Vanderhye P.C.

(57) ABSTRACT

This invention concerns an automatic sampler (AS) associable with two or more chromatographic analysis instruments (GC1, GC2, GCn), such as gas chromatographs for example, which can be interfaced with two or more separate data systems (DS1, DS2, DSn), each operating in an independent manner.

10 Claims, 2 Drawing Sheets

AUTOMATIC SAMPLER ASSOCIABLE WITH CHROMATOGRAPHIC ANALYSIS INSTRUMENTS

This application is the U.S. national phase of international application PCT/IB2005/000441, filed 22 Feb. 2005, which designated the U.S. and claims priority of IT MI2004A000399, filed 3 Mar. 2004, the entire contents of each of which are hereby incorporated by reference.

FIELD OF THE INVENTION

This invention concerns an automatic sampler associable with chromatographic analysis instruments.

PRIOR ART

For a long time now, the use of instruments for the purpose of carrying out the chromatographic analysis of material samples is known. For example, gas chromatographs (GC) and/or liquid chromatographs (LC) are used, etc.

The feeding of such instruments with samples of material to be analyzed is often carried out via an automatic sampler. Automatic samplers are devices able to perform a predetermined sequence of operations on a number of samples to be analyzed, contained in special containers, in order to feed these samples to a certain instrument according to the conditions set for carrying out the analysis. Typically, automatic samplers are equipped with a syringe for taking a sample from the associated container and injecting the treated sample in an input port of a chromatographic analysis instrument. The possible unambiguous identification of the sample to be analyzed can be carried out by reading a bar code, or via another system of identification provided on/in the associated container. For this reason, the samplers can be equipped with a special module for reading bar codes, or another system of identification. Traditional automatic samplers can provide for the treatment of samples to be analyzed through the use of reagents stored in special tanks. Furthermore, the manufacture of automatic samplers equipped with stations for washing the syringes with solvents is known.

Known automatic samplers have been used for a long time for feeding samples to a single chromatographic analysis instrument. In this configuration, a sampler is interfaced with a single data acquisition and processing system (data system) and with the aforesaid instrument. The data systems are complex systems with various functions, amongst which there is that of managing and controlling the automatic sampler and those of acquiring and processing the data obtained from the chromatographic analysis. For example, the data systems can provide for the use of a computer, different interfaces, computer programs, data banks, etc. Data systems, in turn, interact with an operator, who can set the most appropriate sampling sequence, for example, the number of washes to perform for cleaning the syringe, the type and quantity of solvent to use, the sample quantity to be taken, all of the parameters that control the preparation methods of each sample, etc.

When using an automatic sampler according to the aforesaid configuration, the usage time of the sampler itself is less than the total time regarding the chromatography analysis, and therefore it is inactive for part of this analysis time. For this reason, in order to increase the productivity of the same sampler itself, it was thought of using a single sampler in functional association with two instruments, that is a single sampler to feed samples to be analyzed to two chromatographic analysis instruments.

In the case in which a sampler is associated with two instruments, it can be used to feed samples to a second instrument when the first instrument has been fed with a sample to analyze, and is thus occupied in completing the chromatographic analysis. Even in this configuration, the drawbacks encountered in using a traditional sampler are many.

For example, while it is possible for the data system serving the first instrument to control and activate the automatic sampler for the analysis of samples according to a number of sampling sequences, generally, it is not possible for any data system serving the second instrument to change the predetermined sampling sequence for feeding. In practice, with regard to the feeding of the first instrument, the sampler can adopt a different sampling sequence for different groups of samples, or even a sampling sequence for each sample to analyze. Conversely, the feeding of the second instrument is carried out by the sampler with the same sampling sequence for all samples, except for the case in which an operator might change it by taking action on the data system serving the second instrument.

Furthermore, the data regarding the analysis performed on a sample by the first instrument can be associated in an unambiguous manner to that sample, for example by associating the operating parameters used for the analysis and the results thereof to the bar code provided on the sample container or to some other system of unambiguous identification. Instead, with regard to the data concerning the analysis of samples performed by the second instrument, the data system serving it cannot unambiguously associate the data concerning the sample analysis, as it has no control of either the sampler or of any unambiguous identification system associated with the samples. The object of this invention is that of making available an automatic sampler, and a method for its use, which resolve the problems of traditional automatic samplers in an extremely simple and inexpensive manner.

It is also an object of this invention to make available an automatic sampler, and a method for its use, which permit material samples to be fed to two or more separate chromatographic analysis instruments according to sampling sequences that are independent for each instrument, providing for the complete control of an independent data system on each of the two or more instruments fed by the sampler.

In addition, a further object of this invention is that of making available an automatic sampler, and a method for its use, which permit data regarding the samples analysis performed by multiple instruments to be acquired and processed, in such a way that said data are associated in an unambiguous manner to each single identification element of each sample, for example a bar code positioned on the container of said sample or another system of unambiguous identification.

SUMMARY OF THE INVENTION

This and other objects are achieved by this invention, which concerns an automatic sampler of the type that is functionally associable with at least two chromatographic analysis instruments and at least one plurality of containers of samples to be subjected to chromatographic analysis, characterized in that it can be interfaced with two or more independent data systems for data acquisition and processing, and for the control/management of said automatic sampler.

Preferably, the above-mentioned chromatographic analysis instruments are gas chromatographs (GC), and/or liquid chromatographs (LC).

According to one aspect of the present invention, the automatic sampler provides two or more distinct interfaces for interfacing with said two or more data systems (DS1, DS2, ... DSn). These interfaces can be RS-232, LAN (Ethernet TCP/IP Local Area Network), IR (infrared), or even wireless types.

The data systems include one or more computers, equipped with associated interfaces for interfacing with the automatic sampler, and on which suitable computer programs are running.

The sampler in accordance with the invention is equipped with two or more interfaces for interfacing with each of the said chromatographic analysis instruments and, in an independent manner, to two or more data system serving each of the instruments. In this case, these interfaces allow the transmission of interfacing logic signals between two or more instruments and the sampler, so as to enable the synchronization of operations.

According to one embodiment of the present invention, the automatic sampler can also include a bar code reader, or another identification system for the codes associated with the sample containers. There can be various types of codes, such as bar codes for example, or codes transmitted from a transponder attached to each sample container, etc.

The invention also concerns a method for the acquisition and/or processing of data regarding the chromatographic analysis of samples through the control of the above-mentioned automatic sampler, including the steps of:

defining a first sampling sequence on a first of said two or more independent data systems;

defining a second sampling sequence on a second of said two or more independent data systems;

defining an nth sampling sequence on an nth of said two or more independent data systems;

activating said automatic sampler by said first data system, according to said first sampling sequence, for feeding said samples to a first chromatographic analysis instrument, or, in a separate manner, by said second data system, according to said second sampling sequence, for feeding said samples to a second chromatographic analysis instrument, or by said nth data system, according to said nth sampling sequence, for feeding said samples to an nth chromatographic analysis instrument.

According to the invention, the method includes the further step of acquiring and/or processing of data regarding the chromatographic analysis of the samples, said data being obtained with the first, with the second or with the nth sampling sequence from the first, second and nth chromatographic analysis instrument respectively.

Preferably, the method includes the reading of the code associated with the containers via a bar code reader or another possible system of identification. In this way, it is possible to collect the data concerning the chromatographic analysis and/or operational data regarding the automatic sampler and the instruments and/or the sampling sequence set up for said analysis, for each of the samples analyzed by one of the said instruments.

According to this invention, the automatic sampler can be shared by two or more distinct data systems, with evident advantages with regard to the exploitation of the sampler itself and with regard to the management of the data obtained from the analyses performed on two or more instruments.

Furthermore, the sampler in accordance with the present invention allows high repeatability of the results from the analyses performed on various samples via multiple instruments to be achieved, thanks to the possibility it offers of associating the data regarding an analysis with a given sample in an unambiguous manner.

BRIEF DESCRIPTION OF THE DRAWINGS

Further aspects and advantages of this invention will become clearer from the description that follows, provided for illustrative and not limitative purposes, with reference to the enclosed schematic drawings, in which.

DETAILED DESCRIPTION OF SOME PREFERRED EMBODIMENTS OF THE INVENTION

Figure 1:
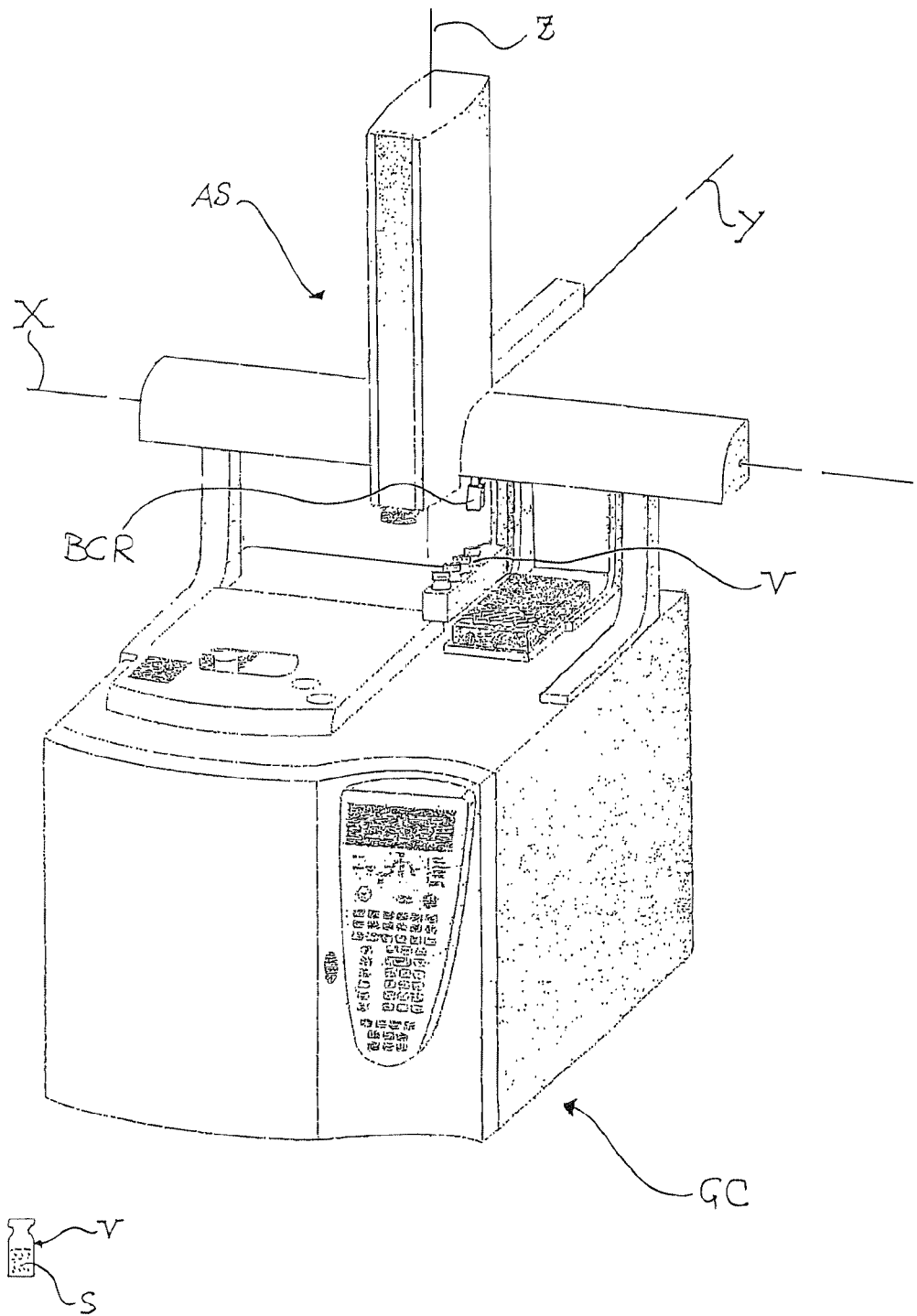
FIG. 1 is a perspective view of an automatic sampler functionally associated with a gas chromatograph.

FIG. 1 illustrates an automatic sampler AS used for feeding samples to be analyzed to an instrument GC for the chromatographic analysis of samples S. In general, the sampler AS according to the invention can be of the X, Y, Z, three-axis type or of another type, and can be associated with two or more instruments GC (GC1, GC2, GC3, etc.).

Although from this point on, reference will be made exclusively to gas chromatographs GC, the invention is not intended to be limited exclusively to these instruments. Generally, in fact, the automatic sampler AS according to this invention can be functionally associated to instruments for liquid chromatographic analysis for example.

Figure 2:
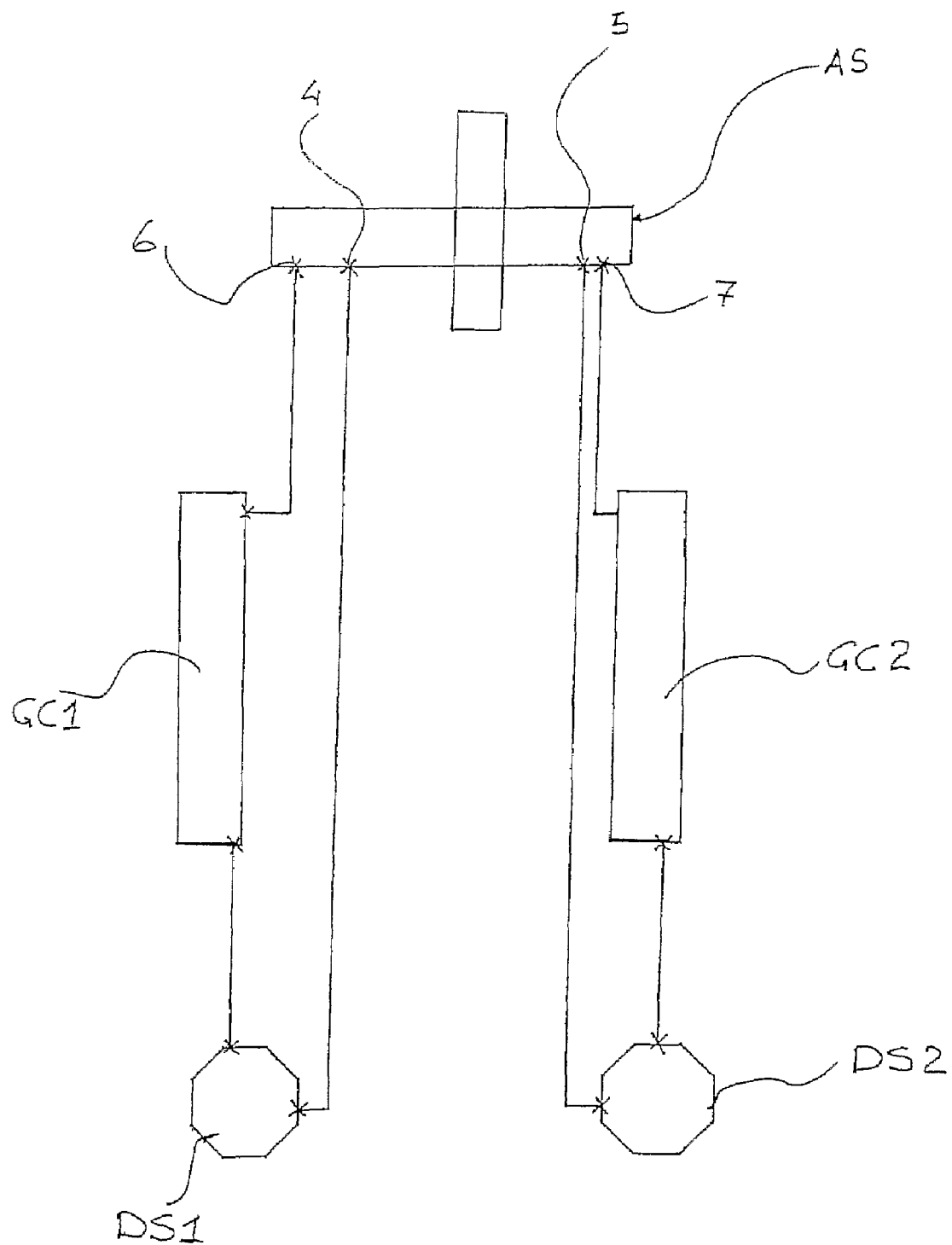
FIG. 2 is a diagram representing the operation of a sampler according to the present invention.

With reference to FIG. 2, the operational diagram of an automatic sampler AS according to this invention is outlined. The sampler is functionally associated with two gas chromatographs GC1 and GC2 positioned, for example, within the radius of action of its syringe. In general, the sampler can be associated with more than two gas chromatographs (GCn).

According to the invention, the automatic sampler AS is equipped with two or more interfaces for interfacing with two or more data systems DS (DS1, DS2, DSn, etc.). In the case outlined in FIG. 2, the sampler is equipped with two interfaces 4 and 5 for interfacing with the first data system DS1 and with the second data system DS2 respectively. The interfaces 4 and 5 can be of different types, of the type known in the art by the acronym RS-232 for example, or they could be of the infrared type, or of the network connection type, via Ethernet TCP/IP LAN for example, or wireless.

The data systems DS1 and DS2 can consist of computer programs and, in practice, share the sampler AS, but operating independently of each other.

An operator can set up different sampling sequences on each data system DS1 or DS2 to be used on the first and on the second gas chromatographs GC1 and GC2 respectively. The independent control of the sampler AS by one of the two data systems DS1 and DS2 allows, in fact, to operate on one of the gas chromatographs GC1 or GC2 without distinction, having the possibility of adopting a data sampling sequence for a given sample and of managing, in an unambiguous manner, the data regarding the analysis performed on that sample. For example, in the case in which the containers V are provided with a distinguishing mark and the automatic sampler AS can recognize this distinguishing mark, the data regarding the chromatographic examination performed on sample S, contained in container V, can be associated, without possibility of error, to that sample S together with the operating parameters adopted by the instrument GC1 or GC2 for the analysis.

The aforesaid distinguishing mark can be a bar code provided, for example, on an adhesive label stuck on the containers V. In this case, the sampler is equipped with a bar code reader BCR. The distinguishing mark can also be a transponder associated with the containers, or a visual type of code (based on colours), etc., in which case the sampler is equipped with a specially provided reader. There are many advantages deriving from the proposed configuration. The sampler AS according to the invention allows high repeatability of the results to be achieved together with an increase in the useful operational time with respect to traditional samplers associated with multiple chromatographic analysis instruments (liquid or gas).

In practice, once the sample S has been identified by the sampler AS, i.e. once an identification code (tag) has been associated with that sample S, for each analysis performed on that sample S by one of the gas chromatographs GC1 or GC2 it is possible to acquire the results of the analyses and the data regarding the conditions under which the analyses were performed (instrument operating parameters, temperatures, pressures, etc.). All these data can be processed by the aforesaid computers and stored.

The sampling sequences that the data systems DS1 and DS2 allow to be set up can include, for example, the number and frequency of washes for the above-mentioned syringe, the type and quantity of solvent to use, the type and quantity of any reagent that must be combined with a sample S, the sample quantity to take, etc.

In order to speed up the operations of the sampler AS, it can also be interfaced with each instrument GC1 and GC2. In the case outlined in FIG. 2, the sampler AS is interfaced with gas chromatograph GC1 via interface 6 and with gas chromatograph GC2 via interface 7. In addition to the traditional logic signals that the gas chromatographs GC1 and GC2 can transmit to the sampler AS, the interfaces 6 and 7 allow the transmission of logic signals such as, for example, stand-by, start, stop, handshake, signals, etc.

The invention claimed is:

1. An automatic sampler associable with at least one plurality of containers of samples to be subjected to chromatographic analysis, automatic samples being interfaced with at least two independent data systems for data acquisition and processing, and for the control/management of said automatic sampler, wherein said data systems serve each of at least two chromatographic analysis systems selected from at least one of gas chromatographic systems and liquid chromatographic systems.

2. An automatic sampler according to claim 1, wherein two or more distinct interfaces are provided for interfacing with said at least two independent data systems.

3. An automatic sampler according to claim 2, wherein said interfaces are of the RS-232, Ethernet TCP/IP LAN, IR, or Wireless type.

4. An automatic sampler according to claim 1, wherein said data systems include one or more computers.

5. An automatic sampler according to claim 1, wherein two or more interfaces are provided for interfacing with each of said chromatographic analysis systems for chromatographic analysis.

6. An automatic sampler according to claim 5, wherein said two or more interfaces allow the transmission of interfacing logic signals between said at least two chromatographic analysis systems and said sampler, so as to enable their synchronization.

7. A method for the acquisition and/or processing of data regarding the chromatographic analysis of samples via the control of an automatic sampler according to claim 1, including the steps of:
  defining a first sampling sequence on a first of said at least two independent data systems;
  defining a second sampling sequence on a second of said at least two independent data systems;
  defining an nth sampling sequence on an nth of said at least two independent data systems; and
  activating said automatic sampler by said first data system, according to said first sampling sequence, for feeding said samples to a first chromatographic analysis system, or, in a separate manner, by said second data system, according to said second sampling sequence, for feeding said samples to a second chromatographic analysis system, or by said nth data system, according to said nth sampling sequence, for feeding said samples to an nth chromatographic analysis system, wherein said first through nth chromatographic analysis systems are selected from gas chromatographic systems and liquid chromatographic systems.

8. A method according to claim 7, further comprising:
  acquiring and/or processing of data regarding the chromatographic analysis of said samples, said data being obtained with said first, with said second or with said nth sampling sequence from said first, said second or said nth chromatographic analysis system.

9. A method according to claim 7, further comprising:
  reading a code associated with the containers of said samples, via a code reader of said automatic sampler.

10. A method according to claim 7, wherein for each of said samples analyzed by one of said systems for chromatographic analysis, the data regarding the chromatographic analysis and/or the operational data regarding said automatic sampler and said systems for chromatographic analysis and/or the sampling sequence set up for said analysis, are acquired.

* * * * *